United States Patent

Nanri et al.

(10) Patent No.: US 9,718,776 B2
(45) Date of Patent: Aug. 1, 2017

(54) FLUORINATED BENZILIC ACID ESTER COMPOUND AND SALT THEREOF

(71) Applicant: TAIHO PHARMACEUTICAL CO., LTD., Tokyo (JP)

(72) Inventors: Masato Nanri, Tokushima (JP); Kazuharu Noguchi, Tokyo (JP); Fukumitsu Sakakibara, Tsukuba (JP); Shinichi Aoki, Saitama (JP)

(73) Assignee: Taiho Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 14/889,042

(22) PCT Filed: May 29, 2014

(86) PCT No.: PCT/JP2014/064216
§ 371 (c)(1),
(2) Date: Nov. 4, 2015

(87) PCT Pub. No.: WO2014/192847
PCT Pub. Date: Dec. 4, 2014

(65) Prior Publication Data
US 2016/0115129 A1 Apr. 28, 2016

(30) Foreign Application Priority Data
May 30, 2013 (JP) .................. 2013-114142

(51) Int. Cl.
*C07D 211/44* (2006.01)
*C07D 211/46* (2006.01)

(52) U.S. Cl.
CPC .......... *C07D 211/44* (2013.01); *C07D 211/46* (2013.01)

(58) Field of Classification Search
CPC ............................ C07D 211/44; A61K 31/445
USPC ........................................... 546/218; 514/317
See application file for complete search history.

(56) References Cited

U.S. PATENT DOCUMENTS

2004/0242887 A1  12/2004 Alken et al.

FOREIGN PATENT DOCUMENTS

| GB | 2031727 A | 4/1980 |
| JP | 555-055117 A | 4/1980 |
| JP | S62-039567 A | 2/1987 |
| JP | S62-051242 B2 | 10/1987 |
| JP | 2004-534802 A | 11/2004 |

OTHER PUBLICATIONS

Wuest et al. "Propiverine and metabolites . . . " Naunyn-Schmeideber's Arch Pharmaco1374, p. 87-97 (2006).*
Laterra et al. "Blood brain barrier" Basic Neurochemisty p. 1-5 (1999).*
Meanwell "Synopsis of some . . . " J. Med. Chem.54, 2529-2591 (2011).*
Patani et al. "Bioisoterism . . . " Chem. Rev. 96, 3147-3176 (1996).*
Scher "fluoride" p. 1-2 (2010).*
Wuest et al. "Pharmacodynamics of propiverine . . . " Br. J. Pharm. 145, p. 608-619 (2005).*
Hunskaar et al., "Epidemiology and Natural History of Urinary Incontinence", International Urogynecology Journal, 2000, vol. 11, No. 5, pp. 301-319.
Fergusson et al., "Association between suicide attempts and selective serotonin reuptake inhibitors: systematic review of randomised controlled trials"; BMJ, 2005, vol. 330, No. 7488, 396.
Search Report cited in PCT/JP2014/064216 dated Aug. 19, 2014 (3 pages).

* cited by examiner

Primary Examiner — Celia Chang
(74) Attorney, Agent, or Firm — Rothwell, Figg, Ernst & Manbeck, P.C.

(57) ABSTRACT

A benzilic acid ester compound represented by the following formula (I) or a salt thereof,

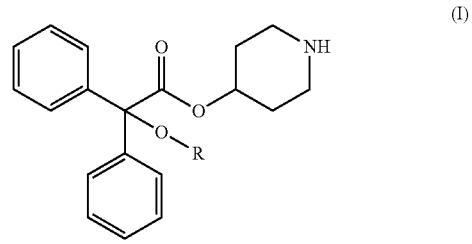

wherein R represents optionally substituted fluorinated lower alkyl, is disclosed.

12 Claims, 1 Drawing Sheet

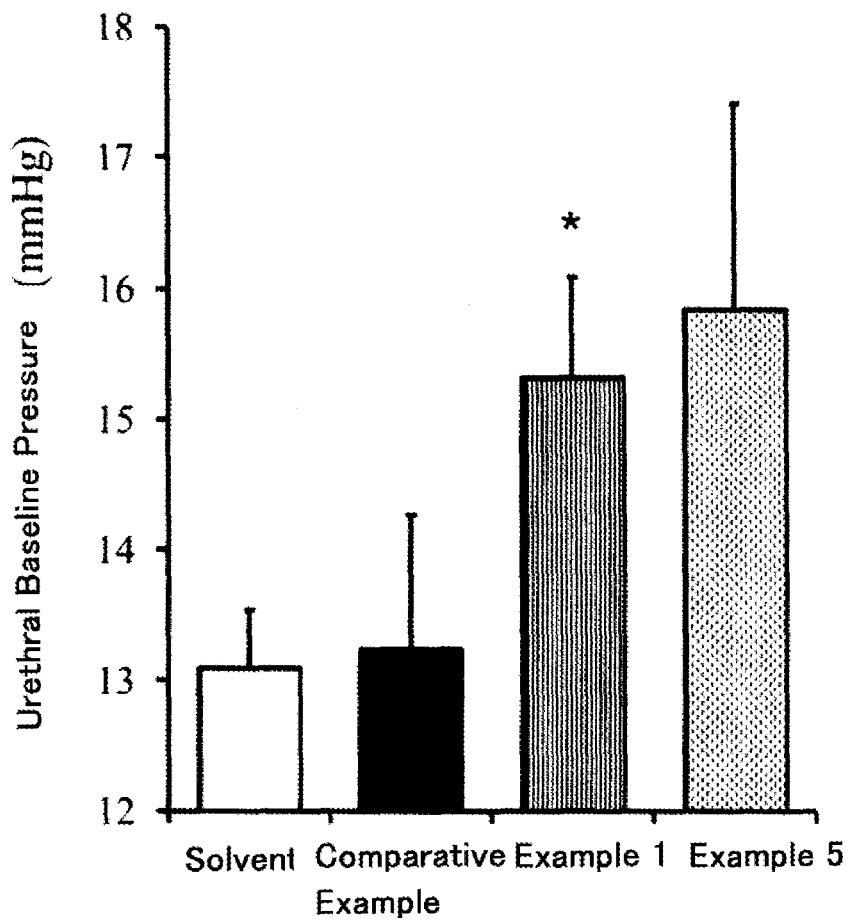
Each column is indicated as mean ± SE of 7 or 8 rats.
*: $P<0.05$.

FLUORINATED BENZILIC ACID ESTER COMPOUND AND SALT THEREOF

This application is a 35 U.S.C. 37 National Phase Entry Application from PCT/2014/064216, filed May 29, 2014, which claims priority to Japanese Patent Application No. 2013-114142, filed on May 30, 2013, the entire contents of which are herein incorporated by reference.

TECHNICAL FIELD

The present invention relates to a fluorinated benzilic acid ester compound or a salt thereof that is useful for a prophylactic and/or therapeutic agent for a disease that is expected to be ameliorated by an increase in intraurethral pressure, such as stress urinary incontinence.

BACKGROUND ART

Urinary incontinence is involuntary leakage of urine, and pathological urinary incontinence is a condition in which objective leakage, which is a social or hygienic problem, is observed. Stress urinary incontinence is leakage of urine upon a rise in abdominal pressure, such as during coughing, sneezing, laughing, or exercising, despite the absence of bladder contraction. Stress urinary incontinence has two main causes. One is hypermobility of the bladder neck and urethra. Descent of the bladder neck due to pelvic floor relaxation causes poor transmission of abdominal pressure to the urethra. Thus, upon a rise in abdominal pressure, only intravesical pressure is increased, resulting in leakage of urine. The other is intrinsic sphincter deficiency, leakage of urine upon a rise in abdominal pressure due to reduced sphincter function. Examples of the causes thereof include childbirth, obesity, aging, menopause, and pudendal nerve injury. Stress urinary incontinence is the most common type of urinary incontinence, and is reportedly observed in about 50% of female patients with urinary incontinence (Non-patent Literature 1). Urinary incontinence has significant adverse effects on women physically, mentally, and socially; inhibits participation in sports or social activities; and becomes a factor that decreases the quality of daily life (QOL). As a result, patients with stress urinary incontinence are made to suffer in their daily lives.

In recent years, duloxetine, a serotonin-noradrenaline reuptake inhibitor (SNRI), has been developed and used as a new therapeutic agent for stress urinary incontinence in Europe. However, since duloxetine also has an antidepressant action, and there are concerns about side effects such as suicide (Non-patent Literature 2), duloxetine has not been approved as a therapeutic agent for stress urinary incontinence in other countries, including the United States and Japan. Therefore, there is a demand for the development of drugs that are useful for stress urinary incontinence.

Patent Literature 1 to 3 describe benzilic acid ester compounds.

CITATION LIST

Patent Literature

PTL 1: JPS62-051242B
PTL 2: JP2004-534802A
PTL 3: JPS62-039567A

Non-Patent Literature

NPL 1: Int Urogynecol J Pelvic Floor Dysfunct (2000), 11 (5), 301-319
NPL 2: Bmj (2005), 330 (7488), 396

SUMMARY OF INVENTION

Technical Problem

An object of the present invention is to provide a drug that is useful for a disease that is expected to be ameliorated by an increase in intraurethral pressure, such as stress urinary incontinence.

Solution to Problem

The present inventors conducted extensive research on compounds having an effect of ameliorating stress urinary incontinence, and found that a fluorinated benzilic acid ester compound represented by the following formula (I) has an intraurethral pressure-increasing action. The inventors conducted further research, and accomplished the present invention.

The present invention provides the following benzilic acid ester compound or a salt thereof and a prophylactic and/or therapeutic agent for a disease that is expected to be ameliorated by an increase in intraurethral pressure, such as stress urinary incontinence, the agent comprising the benzilic acid ester compound or a salt thereof as an active ingredient.

Item 1. A benzilic acid ester compound represented by the following formula (I) or a salt thereof,

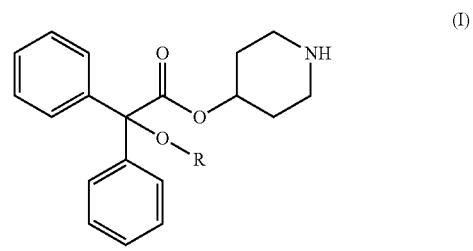

wherein R represents optionally substituted fluorinated lower alkyl.

Item 2. The benzilic acid ester compound according to item 1 or a salt thereof, wherein R represents fluorinated straight $C_{1-6}$ alkyl.

Item 3. The benzilic acid ester compound according to item 1 or 2 or a salt thereof, wherein R represents n-propyl in which 2 to 7 of the hydrogen atoms are replaced by fluorine.

Item 4. The benzilic acid ester compound according to any of items 1 to 3 or a salt thereof, wherein R represents 3,3,3-trifluoropropyl, 3-fluoropropyl, 3,3-difluoropropyl, 2,2-difluoroethyl, 2,2,3,3-tetrafluoropropyl, or 2,2,3,3,3-pentafluoropropyl.

Item 5. A benzilic acid ester compound of any of the following (a) to (f), or a salt thereof:

(a) 4-piperidinyl 2,2-diphenyl-2-(3,3,3-trifluoropropoxy)acetate,
(b) 4-piperidinyl 2,2-diphenyl-2-(3-fluoropropoxy)acetate,
(c) 4-piperidinyl 2,2-diphenyl-2-(3,3-difluoropropoxy)acetate,
(d) 4-piperidinyl 2,2-diphenyl-2-(2,2-difluoroethoxy)acetate, (e) 4-piperidinyl 2,2-diphenyl-2-(2,2,3,3-tetrafluoropropoxy)acetate, and (f) 4-piperidinyl 2,2-diphenyl-2-(2,2,3,3,3-pentafluoropropoxy)acetate.

Item 6. A pharmaceutical composition comprising an effective amount of the benzilic acid ester compound according to any of items 1 to 5 or a salt thereof, and a pharmaceutical carrier.

Item 7. A prophylactic and/or therapeutic agent for a disease that is expected to be ameliorated by an increase in intraurethral pressure, the agent comprising an effective amount of the benzilic acid ester compound according to any of items 1 to 5 or a salt thereof, and a pharmaceutical carrier.

Item 8. A prophylactic and/or therapeutic agent for stress urinary incontinence, the agent comprising an effective amount of the benzilic acid ester compound according to any of items 1 to 5 or a salt thereof, and a pharmaceutical carrier.

Item 9. A method for preventing and/or treating a disease that is expected to be ameliorated by an increase in intraurethral pressure, the method comprising administering an effective amount of the benzilic acid ester compound according to any of items 1 to 5 or a salt thereof.

Item 10. The method according to item 9, wherein the disease that is expected to be ameliorated by an increase in intraurethral pressure is stress urinary incontinence.

Item 11. The benzilic acid ester compound according to any of items 1 to 5 or a salt thereof for preventing and/or treating a disease that is expected to be ameliorated by an increase in intraurethral pressure.

Item 12. Use of the benzilic acid ester compound according to any of items 1 to 5 or a salt thereof for preventing and/or treating a disease that is expected to be ameliorated by an increase in intraurethral pressure.

Item 13. Use of the benzilic acid ester compound according to any of items 1 to 5 or a salt thereof for the production of a prophylactic and/or therapeutic agent for a disease that is expected to be ameliorated by an increase in intraurethral pressure.

Advantageous Effects of Invention

The present invention provides a fluorinated benzilic acid ester compound represented by formula (I) above or a salt thereof, which is useful as a prophylactic and/or therapeutic agent for stress urinary incontinence.

It has been revealed that the benzilic acid ester compound or a salt thereof of the present invention exhibits an excellent intraurethral pressure-increasing action in vivo. Accordingly, the benzilic acid ester compound or a salt thereof of the present invention can be expected to have efficacy as a prophylactic and/or therapeutic agent for a disease that is expected to be ameliorated by an increase in intraurethral pressure, such as stress urinary incontinence.

BRIEF DESCRIPTION OF DRAWINGS

FIG. 1 shows changes in urethral baseline pressure 8 hours after administration of test substances.

DESCRIPTION OF EMBODIMENTS

In the present invention, the term "therapeutic" or "treatment" means a cure or amelioration of a disease or symptom, or suppression of a symptom; the term encompasses "prevention." The term "prophylactic" or "prevention" means prevention of the expression of a disease or symptom.

The benzilic acid ester compound of the present invention is a fluorinated benzilic acid ester compound represented by the following formula (I) or a salt thereof,

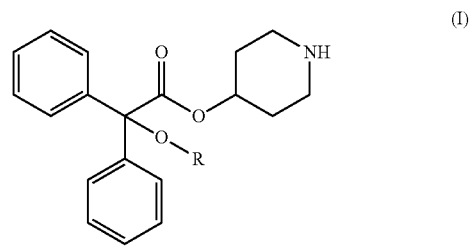

wherein R represents optionally substituted fluorinated lower alkyl.

The benzilic acid ester compound of the present invention, which is represented by formula (I) above, is a novel compound that is not specifically disclosed in, for example, the aforementioned literature.

For example, Patent Literature 1 (JPS62-051242B) discloses an α,α-diphenyl-α-alkoxyacetic acid-1-methyl-4-piperidyl ester derivative as a compound that can effectively treat hypertonic functional states in the region of the bladder. However, this compound differs from the compound of the present invention in that it has methyl at the 1-position of piperidine and in that it is not fluorinated.

Patent Literature 2 (JP2004-534802A) discloses deuterated N- and α-substituted diphenyl alkoxy acetic acid aminoalkyl esters that are useful as pharmaceutical preparations for treating hypertonic functional states. However, they differ from the compound of the present invention in that they have methyl at the 1-position of piperidine, and in that they are not fluorinated but deuterated.

Further, Patent Literature 3 (JPS62-039567A) discloses a benzilic acid 4 piperidyl ester derivative having a bladder capacity-increasing action. However, this compound differs from the compound of the present invention in that it is not fluorinated, and in that it did not have a significant effect on urethral baseline pressure, as shown in the Test Example (Comparative Example) described later.

In the present specification, the lower alkyl of "optionally substituted fluorinated lower alkyl" represented by R is straight or branched $C_{1-6}$ alkyl. Examples thereof include methyl, ethyl, n-propyl, isopropyl, n-butyl, isobutyl, sec-butyl, tert-butyl, n-pentyl, n-hexyl, and the like. Straight $C_{1-6}$ alkyl is preferable, and n-propyl is more preferable.

Examples of substituents of "optionally substituted fluorinated lower alkyl" represented by R include chlorine atom, bromine atom, iodine atom, hydroxyl, cyano, amino, nitro, oxo, carboxyl, carbamoyl, cycloalkyl (such as cyclopropyl, cyclobutyl, cyclopentyl, and cyclohexyl), alkenyl (such as vinyl, 1- or 2-propenyl, and 1-butenyl), alkynyl (such as ethynyl, 1- or 2-propynyl, 1-, 2-, or 3-butynyl, and 1-methyl-2-propynyl), alkoxy (such as methoxy, ethoxy, propoxy, isopropoxy, butoxy, isobutoxy, tert-butoxy, pentyloxy, isopentyloxy, and hexyloxy), acyl (such as formyl, acetyl, propionyl, butynyl, isobutynyl, and benzoyl), acyloxy (such as formyloxy, acetyloxy, propionyloxy, butynyloxy, isobutynyloxy, and benzoyloxy), alkoxycarbonyl (such as methoxycarbonyl, ethoxycarbonyl, propoxycarbonyl, isopropoxycarbonyl, butoxycarbonyl, isobutoxycarbonyl, tert-butoxycarbonyl, pentyloxycarbonyl, isopentyloxycarbonyl, and hexyloxycarbonyl), saturated heterocyclic groups (such as azetidino, pyrrolidino, imidazolidino, oxazolidino, thiazolidino, piperazino, piperidino, morpholino, and thiomorpholino), unsaturated heterocyclic groups (such as furyl, thienyl, pyrrolyl, imidazolyl, pyrazolyl, oxazolyl, thiazolyl, isoxazolyl, isothiazolyl, pyridyl, pyrazinyl, pyrimidinyl, pyridazinyl, indolyl, quinolyl, isoquinolyl, benzo[b]thienyl, and benzimidazolyl), aromatic hydrocarbon groups (such as phenyl, naphthyl, tolyl, xylyl, anthracenyl, phenanthrenyl, and biphenylyl), alkylamino (such as methylamino, ethylamino, n-propylamino, isopropylamino, n-butylamino, isobutylamino, sec-butylamino, tert-butylamino, n-pentylamino, and n-hexylamino), acylamino (such as formylamino, acetylamino, propionylamino, butynylamino, isobutynylamino, and benzoylamino), aralkyloxy (such as benzyloxy, phenethyloxy, phenylpropyloxy, and naphthylmethyloxy), and the like. Hydroxyl is preferable. When such substituents are present, the number thereof is typically one to three.

In the present specification, the term "fluorinated" indicates that one to all of the hydrogen atoms of R are replaced by fluorine, and preferably indicates that two to seven of the hydrogen atoms of R are replaced by fluorine.

The optionally substituted fluorinated lower alkyl is particularly preferably 3,3,3-trifluoropropyl, 3-fluoropropyl, 3,3-difluoropropyl, 2,2-difluoroethyl, 2,2,3,3-tetrafluoropropyl, or 2,2,3,3,3-pentafluoropropyl.

The benzilic acid ester compound of the present invention can be produced according to reaction scheme 1 below.

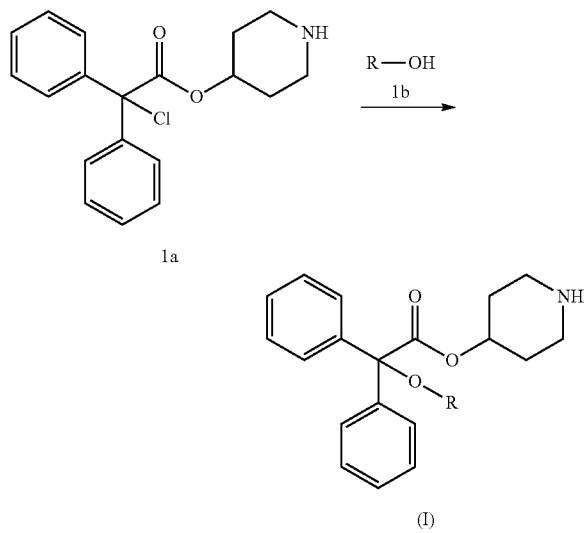

Reaction Scheme 1

(in reaction scheme 1 above, R is the same as above.)

The compound represented by formula (I) can be obtained by reacting the compound represented by formula (1a) with the compound represented by formula (1b) in a suitable solvent. The compound represented by formula (1a) can be produced, for example, by the method disclosed in Pharmazie (1988), 43 (2), 86-90 and may be an acid addition salt with an inorganic acid, such as hydrochloric acid, hydrobromic acid, hydroiodic acid, sulfuric acid, nitric acid, and phosphoric acid, or an acid addition salt with an organic acid, such as formic acid, acetic acid, propionic acid, oxalic acid, malonic acid, succinic acid, fumaric acid, maleic acid, lactic acid, malic acid, citric acid, tartaric acid, carbonic acid, picric acid, methanesulfonic acid, paratoluenesulfonic acid, and glutamic acid. The compound represented by formula (1b) is commercially available.

The solvent used in reaction scheme 1 is not particularly limited as long as it is inert to the reaction. Examples of the solvent include ethers, such as diethyl ether and tetrahydrofuran; esters, such as ethyl acetate and butyl acetate; halogenated hydrocarbons, such as methylene chloride and chloroform; aromatic hydrocarbons, such as benzene, toluene, and chlorobenzene; aprotic polar solvents, such as N,N-dimethylformamide, N,N-dimethylacetamide, dimethyl sulfoxide, and acetonitrile; and alkylketones, such as acetone and methyl ethyl ketone. These may be used alone or in a combination of two or more. In this reaction, an acid may be added. The acid is preferably hydrochloric acid, sulfuric acid, methanesulfonic acid, or paratoluenesulfonic acid, and may be preferably used in an amount of about 1- to about 2-fold molar amount based on the compound represented by formula (1a).

In this reaction, the compound represented by formula (1b) is used in an amount of about 1- to about 20-fold molar amount, and preferably about 1- to about 5-fold molar amount, based on the compound represented by formula (1a). As the solvent, the compound represented by formula (1b) may be used. The reaction temperature is about 50 to about 200° C., and preferably about 80 to about 120° C. The reaction proceeds advantageously in a reaction time of about 1 to about 240 hours.

If one or more asymmetric carbons are present in the compound (I), which is useful as an active ingredient of the medicine of the present invention, optical isomers due to asymmetric carbon atoms (enantiomers and diastereomers) and other isomers may be present. The present invention encompasses each isomer that has been isolated, and mixtures thereof.

The compound (I), which is useful as an active ingredient of the medicine of the present invention, encompasses pharmaceutically acceptable prodrugs. Pharmaceutically acceptable prodrugs are compounds having functional groups that can be converted, under chemical conditions, such as solvolysis, or under physiological conditions, into amino, hydroxyl, carboxyl, carbonyl, or like functional groups of the compound (I), which is an active ingredient of the medicine of the present invention. Representative functional groups of prodrugs include the groups mentioned in "*Iyakuhin no Kaihatsu* [Development of Pharmaceuticals]," Vol. 7, pp. 163-198, Hirokawa Publishing (1990).

The compound (I), which is useful as an active ingredient of the medicine of the present invention, may form an acid addition salt. Such a salt is included in the present invention insofar as it is pharmaceutically acceptable.

Specific examples thereof include acid addition salts with inorganic acids, such as hydrochloric acid, hydrobromic acid, hydroiodic acid, sulfuric acid, nitric acid, and phosphoric acid, or organic acids, such as formic acid, acetic acid, propionic acid, oxalic acid, malonic acid, succinic acid, fumaric acid, maleic acid, lactic acid, malic acid, citric acid, tartaric acid, carbonic acid, picric acid, methanesulfonic acid, paratoluenesulfonic acid, and glutamic acid.

The present invention further encompasses the hydrates, solvates, and crystal polymorphs of the compound (I), which is useful as an active ingredient of the medicine of the present invention, and pharmaceutically acceptable salts thereof.

The compound (I) useful as an active ingredient of the present invention may be used for mammals including humans (for example, humans, cattle, horses, pigs, monkeys, dogs, cats, mice, rats, rabbits, goats, sheep and the like), and preferably for humans.

When a pharmaceutical composition contains the benzilic acid ester compound or a salt thereof of the present invention, a pharmaceutical carrier can be added, if required, thereby forming a suitable dosage form according to prevention or treatment purposes. Examples of the dosage form include oral preparations, injections, suppositories, ointments, patches, and the like. Of these, oral preparations are preferable. Such dosage forms can be formed by common preparation methods known to persons skilled in the art.

As the pharmaceutical carrier, various organic or inorganic carrier materials commonly used as preparation materials may be blended as an excipient, binder, disintegrant, lubricant, or colorant in solid preparations; or as a solvent, solubilizing agent, suspending agent, isotonizing agent, buffer, or soothing agent in liquid preparations. Moreover, a pharmaceutical preparation additive, such as an antiseptic, antioxidant, colorant, sweetener, and stabilizer, may also be used, if required.

Oral solid preparations can be prepared as follows. An excipient, optionally together with a binder, disintegrant, lubricant, colorant, sweetening/flavoring agent, or the like, is added to the compound of the present invention to produce tablets, coated tablets, granules, powders, capsules, or the like, using an ordinary method.

Examples of excipients include lactose, sucrose, D-mannitol, glucose, starch, calcium carbonate, kaolin, microcrystalline cellulose, silicic acid anhydride, and the like.

Examples of binders include water, ethanol, 1-propanol, 2-propanol, simple syrup, liquid glucose, liquid α-starch, liquid gelatin, D-mannitol, carboxymethyl cellulose, hydroxypropyl cellulose, hydroxypropyl starch, methyl cellulose, ethyl cellulose, shellac, calcium phosphate, polyvinylpyrrolidone, and the like.

Examples of disintegrants include dry starch, sodium alginate, agar powder, sodium hydrogen carbonate, calcium carbonate, sodium lauryl sulfate, stearic acid monoglyceride, lactose, and the like.

Examples of lubricants include purified talc, sodium stearate, magnesium stearate, borax, polyethylene glycol, and the like.

Examples of colorants include titanium oxide, iron oxide, and the like.

Examples of sweetening/flavoring agents include sucrose, wild orange peel, citric acid, tartaric acid, and the like.

Oral liquid preparations can be produced as follows. A sweetening/flavoring agent, buffer, stabilizer, or the like, is added to the compound of the present invention to produce an internal liquid medicine, a syrup, an elixir, or the like, using an ordinary method. In this case, sweetening/flavoring agents as described above are usable. Examples of buffers include sodium citrate and the like, and examples of stabilizers include tragacanth, gum arabic, gelatin, and the like. If necessary, an enteric coating or a coating to increase the persistence of effects can be provided by methods known for oral preparations. Examples of coating agents include hydroxypropyl methylcellulose, ethyl cellulose, hydroxymethyl cellulose, hydroxypropyl cellulose, polyoxy ethylene glycol, Tween 80 (registered trademark), and the like.

Injections can be prepared as follows. A pH adjuster, buffer, stabilizer, isotonizing agent, topical anesthetic, or the like, is added to the compound of the present invention to produce a subcutaneous injection, an intramuscular injection, or an intravenous injection using an ordinary method. Examples of pH adjusters and buffers usable in this case include sodium citrate, sodium acetate, sodium phosphate, and the like. Examples of stabilizers include sodium pyrosulfite, EDTA, thioglycolic acid, thiolactic acid, and the like. Examples of topical anesthetics include procaine hydrochloride, lidocaine hydrochloride, and the like. Examples of isotonizing agents include sodium chloride, glucose, D-mannitol, glycerin, and the like.

Suppositories can be prepared as follows. A pharmaceutical carrier known in the art, such as polyethylene glycol, lanolin, cacao butter, or fatty acid triglyceride, is added to the compound of the present invention, optionally together with a like surfactant, such as Tween 80 (registered trademark), followed by production using an ordinary method.

Ointments can be prepared as follows. An ordinary base, stabilizer, wetting agent, preservative, or the like, is added as required to the compound of the present invention, and mixed and formulated using an ordinary method. Examples of bases include liquid paraffin, white petrolatum, white beeswax, octyldodecyl alcohol, paraffin, and the like. Examples of preservatives include methyl parahydroxybenzoate, ethyl parahydroxybenzoate, propyl parahydroxybenzoate, and the like.

Patches can be prepared by coating a general support with the above ointment, cream, gel, paste, or the like, using an ordinary method. Examples of supports include woven or nonwoven fabrics made from cotton, staple fibers, and chemical fibers; and films and foam sheets of soft vinyl chloride, polyethylene, and polyurethane.

The amount of the compound of the present invention to be contained in such a dosage unit form varies depending on the condition of the patient or on the dosage form. The desirable amount in one dosage unit form is typically about 0.05 to about 1,000 mg in the case of an oral preparation, about 0.01 to about 500 mg in the case of an injection, and about 1 to about 1,000 mg in the case of a suppository.

The daily dose of a medicine in such a dosage form depends on the condition, body weight, age, gender, or the like, of the patient. For example, the daily dose for an adult (body weight: 50 kg) may be generally about 0.05 to about 5,000 mg, and preferably 0.1 to 1,000 mg, and is preferably administered in one dose or in two to three divided doses per day.

Administration of a medicine containing the compound of the present invention is useful, for example, in mammals, and in particular humans, for preventing or treating a disease that is expected to be ameliorated by an increase in intraurethral pressure. Examples of diseases that can be treated, prevented, or ameliorated with a medicine containing the compound of the present invention include stress urinary incontinence, urge urinary incontinence, mixed urinary incontinence, and urinary incontinence after an operation to remove the entire prostate gland. Further, a medicine containing the compound of the present invention is also useful for frequent urination and urinary incontinence in neurogenic bladder, nervous bladder, unstable bladder, bladder irritation (chronic cystitis and chronic prostatitis), or the like; urinary urgency and frequent urination in overactive bladder; cardiovascular disease; irritable bowel syndrome; and climacteric disorder.

EXAMPLES

Examples and a Test Example are given below to illustrate the present invention in more detail; however, the present invention is not limited to these Examples.

Reference Example 1

4-Piperidinyl 2-chloro-2,2-diphenylacetate hydrochloride

Thionyl chloride (3.1 ml, 42.1 mmol) and several drops of dimethylformamide were added to 4-piperidinyl 2-hydroxy-2,2-diphenylacetate hydrochloride (3.00 g, 8.62 mmol) obtained according to the method disclosed in the document Pharmazie (1988), 43 (2), 86-90, and the mixture was stirred for 2 hours at 80° C. The reaction mixture was allowed to cool, and then concentrated under reduced pressure to give 4-piperidinyl 2-chloro-2,2-diphenylacetate hydrochloride. This compound was used for the next reaction without purification.

Example 1

4-piperidinyl 2,2-diphenyl-2-(3,3,3-trifluoropropoxy)acetate hydrochloride 3,3,3-trifluoropropanol (25.0 g, 1.10 mol) was added to the compound obtained in Reference Example 1, and the mixture was stirred while heating under reflux for 100 hours. The reaction mixture was allowed to cool, and then concentrated under reduced pressure. The precipitated solid was collected by filtration, thereby obtaining crude crystals. Subsequently, the obtained crude crystals were recrystallized using ethyl acetate and 2-propanol to give the title compound (13.6 g, 56%) as a white solid.

Example 2

4-piperidinyl 2,2-diphenyl-2-(3-fluoropropoxy)acetate hydrochloride

Following the procedure of Example 1, 3-fluoropropanol was used instead of 3,3,3-trifluoropropanol, thereby obtaining the title compound as a white solid.

Example 3

4-piperidinyl 2-(3,3-difluoropropoxy)acetate hydrochloride

Following the procedure of Example 1, 3,3-difluoropropanol was used instead of 3,3,3-trifluoropropanol, thereby obtaining the title compound as a white solid.

Example 4

4-piperidinyl 2,2-diphenyl-2-(2,2-difluoroethoxy)acetate hydrochloride

Following the procedure of Example 1, 2,2-difluoroethanol was used instead of 3,3,3-trifluoropropanol, thereby obtaining the title compound as a white solid.

Example 5

4-piperidinyl 2,2-diphenyl-2-(2,2,3,3-tetrafluoropropoxy)acetate hydrochloride Following the procedure of Example 1, 2,2,3,3-tetrafluoropropanol was used instead of 3,3,3-trifluoropropanol, thereby obtaining the title compound as a white solid.

Example 6

4-piperidinyl 2,2-diphenyl-2-(2,2,3,3,3-pentafluoropropoxy)acetate hydrochloride Following the procedure of Example 1, 2,2,3,3,3-pentafluoropropanol was used instead of 3,3,3-trifluoropropanol, thereby obtaining the title compound as a white solid.

TABLE 1

| Example | R | 1H-NMR (DMSO-d6) δ (ppm) | m.p. (° C.) |
|---|---|---|---|
| 1 | —CH$_2$—CH$_2$—CF$_3$ | 1.63-1.69 (m, 2H), 1.87-1.94 (m, 2H), 2.48-2.57 (m, 2H), 2.75-2.90 (m, 2H), 2.95-3.05 (m, 2H), 3.38-3.43 (m, 2H), 5.05-5.08 (m, 1H), 7.34-7.41 (m, 10H), 8.65 (brs, 1H) | 152-153 |
| 2 | —CH$_2$—CH$_2$—CH$_2$F | 1.63-1.69 (m, 2H), 1.82-1.94 (m, 2H), 2.80-2.85 (m, 2H), 2.96-2.3.02 (m, 2H), 3.25-3.32 (m, 2H), 4.46-4.50 (m, 1H), 4.58-4.62 (m, 1H), 5.03-5.06 (m, 1H), 7.31-7.40 (m, 10H), 8.67 (brs, 1H) | 135-136 |
| 3 | —CH$_2$—CH$_2$—CHF$_2$ | 1.64-1.69 (m, 2H), 1.90-1.99 (m, 2H), 2.06-2.10 (m, 2H), 2.78-2.82 (m, 2H), 2.95-3.01 (m, 2H), 3.29-3.34 (m, 2H), 5.05-5.08 (m, 1H), 6.02-6.37 (m, 1H), 7.32-7.40 (m, 10H), 8.78 (brs, 1H) | 130-132 |
| 4 | —CH$_2$—CHF$_2$ | 1.66-1.70 (m, 2H), 1.89-1.97 (m, 2H), 2.65-2.75 (m, 2H), 2.95-3.05 (m, 2H), 3.39-3.46 (m, 2H), 5.03-5.08 (m, 1H), 5.95-6.29 (m, 1H), 7.33-7.42 (m, 10H), 8.65 (brs, 1H) | 172-174 |
| 5 | —CH$_2$—CF$_2$—CHF$_2$ | 1.63-1.71 (m, 2H), 1.89-2.02 (m, 2H), 2.75-2.85 (m, 2H), 2.95-3.05 (m, 2H), 3.65-3.72 (m, 2H), 5.06-5.12 (m, 1H), 6.49-6.75 (m, 1H), 7.33-7.44 (m, 10H), 8.65 (brs, 1H) | 128-130 |

TABLE 1-continued

| Example | R | 1H-NMR (DMSO-d6) δ (ppm) | m.p. (° C.) |
|---|---|---|---|
| 6 | —CH$_2$—CF$_2$—CF$_3$ | 1.62-1.70 (m, 2H), 1.89-1.99 (m, 2H), 2.78-2.84 (m, 2H), 2.95-3.05 (m, 2H), 3.84-3.90 (m, 2H), 5.07-5.11 (m, 1H), 7.32-7.46 (m, 10H), 8.64 (brs, 1H) | 98-100 |

Test Example 1

1. Test Method

The compounds of the present invention and a comparative compound were individually orally administered in an amount of 10 mg/kg to 11-week-old female SD rats (test substance-administration groups) and distilled water was orally administered as the control to 11-week-old female SD rats (solvent administration group, n=8). As the comparative compound, 4-piperidyl 2,2-diphenyl-2-propoxyacetate was used (Comparative Example).

Seven and a half hours after administration, each rat was anesthetized by intraperitoneal administration of 1.2 g/kg of urethane. Thereafter, the ureters and the area between the urethra and the bladder were ligated, and a vesical fistula catheter and a catheter for measuring intraurethral pressure were inserted and indwelled in the bladder and the urethra. The catheter for measuring intraurethral pressure was inserted from the external urethral orifice. The other end of each catheter was connected to a corresponding pressure transducer branched into two directions via a corresponding three-way stopcock, and the remaining connecting portion of each three-way stopcock was connected to a corresponding syringe set in a continuous injection device. Intravesical pressure and intraurethral pressure were recorded via a polygraph connected with the pressure transducers. After the operation, physiological saline is injected into the bladder using the micro syringe pump connected to the bladder, and the injection was stopped when rhythmic bladder contraction was observed. Physiological saline was injected into the urethra using the micro syringe pump connected to the urethra at 3 mL/hr, and the changes in intraurethral pressure associated with the rhythmic contraction were recorded.

2. Evaluation Item and Statistical Analysis

The mean value of urethral baseline pressure for each rat, i.e., intraurethral pressure in a state in which the bladder does not contract, for 30 minutes after 8 hours from the administration, was calculated. The mean values of the urethral baseline pressure for the solvent administration group and the test substance-administration groups were calculated, and the results were indicated as mean±SE. A Student's t-test was used for the comparison between the solvent administration group and the test substance-administration groups.

3. Results

FIG. 1 shows the urethral baseline pressure of the solvent administration group and test substance-administration groups. The comparative compound had little effect on the urethral baseline pressure, whereas the compounds of the present invention significantly increased the urethral baseline pressure. Since decrease in urethral baseline pressure is believed to be a cause of stress urinary incontinence, the compounds of the present invention are believed to be useful as a prophylactic or therapeutic agent for a disease that is expected to be ameliorated by an increase in intraurethral pressure, such as stress urinary incontinence.

The invention claimed is:

1. An isolated benzylic acid ester compound represented by the following formula or a salt thereof,

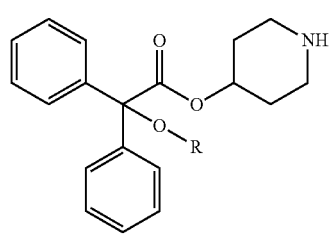

(I)

wherein R represents a fluorinated lower alkyl.

2. The isolated benzylic acid ester compound according to claim 1 or a salt thereof, wherein R represents fluorinated straight $C_{1-6}$ alkyl.

3. The isolated benzylic acid ester compound according to claim 1 or a salt thereof, wherein R represents n-propyl in which 2 to 7 of the hydrogen atoms are replaced by fluorine.

4. The isolated benzylic acid ester compound according to claim 1 or a salt thereof, wherein R represents 3,3,3-trifluoropropyl, 3-fluoropropyl, 3,3-difluoropropyl, 2,2-difluoroethyl, 2,2,3,3-tetrafluoropropyl, or 2,2,3,3,3-pentafluoropropyl.

5. An isolated benzylic acid ester compound of any of the following (a) to (f), or a salt thereof:
 (a) 4-piperidinyl 2,2-diphenyl-2-(3,3,3-trifluoropropoxy)acetate,
 (b) 4-piperidinyl 2,2-diphenyl-2-(3-fluoropropoxy)acetate,
 (c) 4-piperidinyl 2,2-diphenyl-2-(3,3-difluoropropoxy)acetate,
 (d) 4-piperidinyl 2,2-diphenyl-2-(2,2-difluoroethoxy)acetate,
 (e) 4-piperidinyl 2,2-diphenyl-2-(2,2,3,3-tetrafluoropropoxy)acetate, and
 (f) 4-piperidinyl 2,2-diphenyl-2-(2,2,3,3,3-pentafluoropropoxy)acetate.

6. A pharmaceutical composition comprising a therapeutically effective amount of a benzylic acid ester compound represented by the following formula or a salt thereof

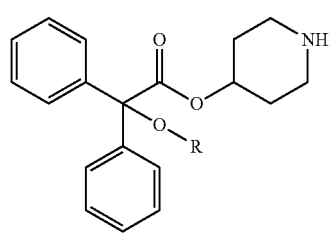

(I)

wherein R represents a fluorinated lower alkyl.

7. The pharmaceutical composition of claim 6, where in the composition is an oral composition.

8. The pharmaceutical composition of claim 7, wherein the composition is a solid oral composition.

9. The pharmaceutical composition of claim 8, wherein the composition is a liquid oral composition.

10. A method for increasing in intraurethral baseline pressure in a patient, the method comprising administering to said patient an effective amount of the benzilic acid ester compound according to claim 1 or a salt thereof.

11. The method according to claim 10, wherein the said patient has been diagnosed with stress urinary incontinence.

12. The method of claim 10 wherein said patient has been diagnosed with stress urinary incontinence, urge urinary incontinence, mixed urinary incontinence, urinary incontinence after an operation to remove the entire prostate gland, frequent urination and urinary incontinence in neurogenic bladder, nervous bladder, unstable bladder, bladder irritation (chronic cystitis and chronic prostatitis), urinary urgency in overactive bladder, or frequent urination in overactive bladder.

\* \* \* \* \*